United States Patent [19]

Visuri

[11] Patent Number: 5,437,993
[45] Date of Patent: Aug. 1, 1995

[54] PREPARATION OF CROSS-LINKED GLUCOSE ISOMERASE CRYSTALS

[75] Inventor: Kalevi Visuri, Kantvik, Finland

[73] Assignee: Strabra AG, Switzerland

[21] Appl. No.: 149,158

[22] Filed: Nov. 8, 1993

Related U.S. Application Data

[60] Continuation of Ser. No. 974,371, Nov. 10, 1992, abandoned, which is a division of Ser. No. 350,720, May 11, 1989, abandoned.

[30] Foreign Application Priority Data

May 13, 1988 [FI]   Finland ................................. 882249

[51] Int. Cl.$^6$ ........................ C12N 9/92; C12N 11/00; C12P 19/24
[52] U.S. Cl. ............................... 435/234; 435/174; 435/94
[58] Field of Search .................... 435/234, 94, 174

[56] References Cited

U.S. PATENT DOCUMENTS

| | | | |
|---|---|---|---|
| 3,980,521 | 9/1976 | Amotz et al. | 435/174 |
| 4,237,231 | 12/1980 | Jackson et al. | 435/234 |
| 4,567,142 | 1/1986 | Lloyd | 435/94 |
| 4,683,203 | 6/1987 | Anton et al. | 435/176 |
| 4,699,882 | 10/1987 | Visuri | 435/188 |
| 5,120,650 | 6/1992 | Visuri | 435/176 |

OTHER PUBLICATIONS

Lee et al., *Bioorganic Chemistry*, vol. 14, 202–210, 1986.
Quiocho et al., NAS Proceedings, vol. 52, 1964.
Bachman et al., Starch/Stärke, 33, Nr. 2, 1981.

*Primary Examiner*—David M. Naff
*Assistant Examiner*—Mike Meller
*Attorney, Agent, or Firm*—Margaret A. Horn

[57] ABSTRACT

The invention relates to a novel water-insoluble glucose isomerase which is formed by a crystalline enzyme converted to solid form by cross-linking. The invention also concerns a process for the preparation of the novel crystalline glucose isomerase by cross-linking with dialdehyde in the presence of a compound containing at least one amino group, and the use of this novel enzyme preparation as an isomerization catalyst. Preferably the compound having an amino group is an ammonium salt, lysine or tryptophan and the dialdehyde is glutaraldehyde.

4 Claims, No Drawings

PREPARATION OF CROSS-LINKED GLUCOSE ISOMERASE CRYSTALS

This is a continuation of application Ser. No. 07/974,371, filed Nov. 10, 1992, now abandoned, which is a divisional of application Ser. No. 07/350,720, filed May 11, 1989, now abandoned.

FIELD OF THE INVENTION

This invention relates to a novel water-insoluble glucose isomerase formed by cross-linking of the crystalline enzyme. The invention is also concerned with a process for the preparation of the insoluble, cross-linked glucose isomerase.

BACKGROUND OF THE INVENTION

The use of immobilized enzymes, i.e., enzymes bound to a solid carrier, in continuously operated reactors is an increasingly preferred technique, since it enables savings in enzyme costs as well as in the purification of the final product. The conversion of glucose to fructose with an immobilized glucose isomerase is a process that commonly utilizes such a procedure.

In general, enzymes are water-soluble, thus making it necessary to use an immobilization technique in a continuous process. The enzyme has to be bound to a solid phase by a method that prevents it from dissolving in the aqueous phase while allowing it to maintain its activity. Various techniques have been suggested to associate enzymes with solid carriers wherein the enzyme is absorbed, covalently linked, cross-linked or microencapsulated. Alternatively, the entire microorganism producing the enzyme can be bound to a solid phase. A good summary of such techniques is presented in e.g. Moo-Young, M. (ed), Comprehensive Biotechnology, 2, Pergamon Press, London 1985, p. 191-211.

In prior processes, the enzyme is bound to a carrier material prepared separately, which as such may be advantageous to the chemical kinetics or the flow technique of the substrate. The carrier material is, however, in most cases more costly than the enzyme acting as a catalyst, especially in large-scale mass production processes, such as those used in the sugar industries. Alternatively, the enzyme can be immobilized by cross-linking it with an inert component, such as gelatin. In any case, the enzyme acting as a catalyst in the prior art forms only a fraction, generally less than 5%, usually 1 to 2%, of the weight and volume of the material used in each particular process.

Other techniques that have been applied include linkage to ion exchangers and absorption to a solid carrier. An example of such an application can be found in U.S. Pat. No. 4,699,882. However, the carrier used in this prior art technique is relatively expensive and the technique requires a large reactor.

The immobilization of enzymes for industrial use entails costs which are not necessarily associated with the used enzyme; they include costs caused by the construction of the process apparatus and the factory premises, carrier material acquisition (reacquisition) costs, cost of disposing of inactivated enzyme material, labor costs caused by emptying and filing reactors (or by the regeneration of the carrier) and secondary costs caused by the slowness of the reactors. As a consequence of long retention times, non-enzymatic, disadvantageous side reactions can often occur, particularly in the production of fructose.

Technically, cross-linking with glutaraldehyde has been of great importance in the immobilization of glucose isomerase. As is known, glutaraldehyde is approved by the FDA for the immobilization of enzymes to be used in food processing.

In addition, the scientific literature includes several examples of the cross-linking of crystalline enzymes by means of glutaraldehyde for basic research purposes. The structure of enzyme crystals is often so weak that the crystals do not withstand the ray beam used in X-ray diffraction studies; however, with glutaraldehyde they can often be stabilized for such purposes. Furthermore, crystals have been cross-linked with the purpose of studying stability and catalysis kinetics. In cases where the cross-linking of crystals has been successful, only glutaraldehyde has been used and the medium has consisted of a solution in which each particular enzyme is maintained in crystalline form. It appears that an insoluble crystal has been formed directly by a reaction between the glutaraldehyde and the enzyme protein. Quiocho and Richards (Proc. Natl. Acad. Sci. (USA) 52 (1964) p. 833 and Biochemistry 5 (1966) p. 4062) were the first to use glutaraldehyde in the cross-linking of carboxypeptidases. Bishop and Richards (J. Mol. Biol. 33 (1968) p. 415–421) have cross-linked crystalline beta lactoglobulin with a 1% aqueous solution of glutaraldehyde at room temperature. The crystals were used for studying the electrical properties of the enzyme. Haas (Biophysic. Journ. 8 (1968) p. 549-555) has cross-linked lysozyme crystals in the presence of a 4% sodium nitrate solution (pH 8), using a glutaraldehyde concentration of 12%.

Dyer, Phillips and Townsend (Thermochimica Acta 8 (1974) p. 456–464) have studied the thermostability of a crystalline carboxypeptidase cross-linked by glutaraldehyde. They have found that cross-linking leads to increased stability. Tuechsen and Ottesen (Carlsberg Res. commun. 42 (1977) p. 407–420) have studied the kinetic properties of a crystalline subtilisin cross-linked by glutaraldehyde in a sodium sulfate solution. With low-molecular substrates, the activity of the crystals was high whereas with high-molecular substrates (that could not diffuse into the crystals) the activity was low.

Wong et al. (Biochem. and Biophysic. Research Communications 80 (1978) p. 886–890) have cross-linked an acidic protease of microbial origin with glutaraldehyde in an ammonium sulfate solution. In the cross-linking, the presence of ammonium sulfate was regarded as a technical disadvantage.

Morozov and Morozova (Biopolymers 20 (1981) p. 451–467) have cross-linked crystalline lysozyme, hemoglobin and myoglobin using 2 to 6% glutaraldehyde solutions and a reaction time of 2 to 10 days at room temperature. Lee et al. (Bioorganic Chemistry 14 (1986) p. 202–210) have cross-linked crystals of alcohol dehydrogenase with glutaraldehyde in the presence of 2-methyl-2,4-pentanediol (25%).

It is often difficult to produce insoluble enzymes by means of glutaraldehyde, especially if the protein contains relatively little lysine. This problem is often circumvented by mixing into the enzyme a protein such as albumen which can be cross-linked to produce an insoluble form (G. B. Broun, Methods in Enzymology, 44 (1976) p. 263). The addition of such an inert foreign protein is not, however, possible when the enzyme to be cross-linked is crystalline. To date, there have been no means of cross-linking in cases where it is not possible to cross-link a crystal to insoluble form by means of glutaraldehyde only.

SUMMARY OF THE INVENTION

As mentioned above, it is known to immobilize glucose isomerase with glutaraldehyde. The isomerase is thereby cross-linked to a support material. Such processes are fully utilized industrially. Attempts to cross-link glucose isomerase crystals to insoluble form, however, are not described in the literature.

It has now been found that it is possible to cross-link glucose isomerase crystals in such a way that the original crystalline state is maintained while the enzymatic activity of the enzyme remains very high. Optimally, the crystalline enzyme has the same activity as that of the original enzyme. The product according to the invention is not soluble in any solvents that might be present when using the enzyme technically. Cross-linked crystalline enzyme can be used as such to fill an isomerization column in a technical isomerization process. By means of the novel cross-linked crystalline enzyme it is possible to carry out a more efficient, continuous isomerization process in columns much smaller than used previously in industrial processes. This is because the present invention enables use of a column filled with pure enzyme, rather than enzyme bound to an inert material which often occupies a majority of the space of the column and accounts for a majority of its cost.

DETAILED DESCRIPTION OF THE INVENTION

In the process according to the invention, glucose isomerase crystals are cross-linked by means of a dialdehyde, such as glutaraldehyde, and a compound containing at least one amino group, such as an ammonium compound, amine, or amino acid, preferably an ammonium salt or lysine. Several amines and amino acids are suitable for use. It is likewise evident that in addition to glutaraldehyde, many other dialdehydes and substances reacting with amino groups, known as cross-linking reagents, can be used in the process.

The activity of a solid crystalline enzyme prepared by means of the process according to the invention is very high. Depending on the conditions used for its production, its activity may be almost the same as that of a free enzyme. Solid crystalline enzyme can be used as such as a column filler in a continuous process. It is extremely stable and withstands mechanical stress well.

If desired, cross-linked crystals can be further bound to form larger bodies, e.g. in spherical, sheetlike, bandlike or the like in shape, in known chemicophysical ways. Enzyme preparations so obtained can withstand various mechanical treatments.

Those skilled in the art will recognize that the cross-linking process, as disclosed herein, can be used to prepare insoluble preparations of virtually any crystalline enzyme which has not, generally because of its amino acid composition, heretofore been found to be conducive to cross-linking.

In the following, the process according to the invention will be described in more detail.

Preparation of Crystalline Glucose Isomerase used as Raw Material

Ammonium sulfate (about 10% by weight) is dissolved in a glucose isomerase solution (1 to 10% by weight of isomerase determined as dry protein). The solution is cooled slowly to about 1° to 2° C. under constant stirring. An essentially complete crystallization of the isomerase thereby occurs (more than 95%). In place of ammonium sulfate, magnesium sulfate or sodium sulfate, for instance, can be used as a crystallization agent. The concentration of the salts used may vary within wide limits, e.g., from 5 to 25% by weight. The time required for the crystallization process also varies within wide limits, e.g., from one hour to several days. In the preparation of large crystals, it is preferable to apply gradual cooling, and the isomerase should be as pure as possible. The crystallization is described in U.S. Pat. No. 4,699,882 (Visuri) which is incorporated herein by reference.

After crystallization the crystal mass is separated by sedimentation or by centrifuging from the mother liquor thereof. If required, the crystal mass is washed with pure solutions of ammonium sulfate, magnesium sulfate or some other substance suitable for crystallization. Cross-linking is carried out on a crystal mass which does not contain any free excess mother liquor and which is sedimented or centrifuged to compact form. A typical activity of such crystal mass is 10,000 GIU/g. It contains 20 to 30% by weight of pure enzyme protein determined as dry substance. It should be noted that enzyme crystals lose their structure if they are dried.

Cross-linking

Crystal mass is suspended in a salt solution such that the crystals will not dissolve therein. The concentration of the enzyme crystals in the solution may vary widely, e.g., 2 to 17% by weight on dry substance.

Ammonium salt is added to the solution if the salt solution does not initially contain ammonium, or a suitable amine or amino acid, such as lysine, is added. The pH of the mixture is adjusted to a value from 5 to 9, preferably from 6 to 8, by adding, for instance, sodium hydroxide solution. Acidity is preferably controlled by a phosphate buffer, e.g., 0.05M sodium phosphate or by automatic pH control with an alkaline solution such as sodium hydroxide. The useful concentration of the added amine or amino acid varies within wide limits and is dependent on the concentration of the other components. The product according to the invention has been prepared with a high yield with amine or amino acid concentrations of 1 to 15% of the final weight of the mixture.

Thereafter glutaraldehyde is added to the mixture for initiating the cross-linking reaction. The amount of glutaraldehyde can be varied within wide limits, from 1 to 45% by weight on wet enzyme crystal mass. The preferred amount depends e.g. on the concentration of the amine contained in the mixture. In general, the preferred concentration varies from 3 to 4.5 g of glutaraldehyde per 3 g of isomerase calculated as dry enzyme. During the reaction the solution is stirred continuously; the temperature ranges from 2° to 25° C. A low temperature is of advantage though the temperature does not seem to be critical. The reaction may occur very rapidly, in a few minutes, especially at higher temperatures. At a low temperature the reaction time may be up to 20 hours.

After the reaction, the insoluble crystals are separated from the mixture by sedimentation or centrifugation. The crystal mass is washed by suspending in water or a suitable salt solution and by recentrifugation. The washing is repeated several times until the crystal mass is sufficiently pure to be used as a catalyst. In connection with the washing it is also preferable to flush off fine-grained precipitate.

It is not advisable to dry the obtained crystal mass if it is to be used as a catalyst in an enzymatic process. Wet crystal mass fully retains its activity for at least six months without any special measures.

Characterization of the Final Product

Cross-linked crystals prepared according to the invention are similar to the original raw material crystals in appearance and size. The size of the crystals is not critical. Crystals having a diameter of 100 to 200 micrometres or larger (up to 1 millimeter) are particularly suited for technical use.

The most important property of the crystals according to the invention is that they are insoluble in water, salt solutions and sugar solutions. It is of particular importance that the isomerase crystals do not dissolve in concentrated solutions of glucose and fructose, even at high temperatures. In industrial processes it is customary to use a temperature of 60° C. and a sugar concentration of 45% by weight. Cross-linked crystals are insoluble under such conditions and at any other sugar concentration and higher temperatures (up to 100° C.). The activity of cross-linked crystals may be within an order of magnitude of the activity of the original enzyme. Technically, it is an advantage and of importance that their activity is many times higher than that of an enzyme immobilized on an inert carrier.

On cross-linking an enzyme in crystalline form, a further advantage is obtained in that the enzyme is stabilized to a notable extent by forces acting in the crystal and naturally keeping together the crystal.

Methods Used for the Characterization of the Starting Material and the Final Product The activity of the isomerase was determined as international glucose isomerase units, abbreviated GIU, per 1 g of a dried enzyme preparation. One unit (GIU) represents an enzyme amount able to convert glucose to fructose at a rate of 1 micromole/min under the following conditions: glucose concentration 2.0 mole/liter, pH 7.0, and temperature 60° C.

For the activity determination, 0.1 to 1 g of an enzyme preparation (original crystal mass or thoroughly washed cross-linked crystal mass) was mixed into a substrate solution (100 ml) such as described above. After a suitable period of time, e.g., 10 minutes, the fructose content of the solution was determined and the activity was calculated and expressed in the above-mentioned units. The amount of enzyme and the reaction time were chosen so that the fructose formed was less than 5% of the total sugar content in order that the measuring result would concern the initial rate of the reaction. The dry content of the starting material and the product were determined by a conventional method by drying the sample at 105° C. to constant weight.

Isomerization Process

Crystalline cross-linked enzyme is suitable for use in a conventional way in a batch isomerization process, whereby the used enzyme is separated after the reaction, e.g., by filtration, and it can be reused, if desired.

On an industrial scale, however, it is to be preferred to carry out the isomerization as a continuous process, whereby the sugar solution to be isomerized is allowed to flow through an enzyme column. By varying the retention time and/or the temperature, the isomerization process is easy to adjust. The enzyme is active within a wide range of temperatures, from the freezing point up to temperatures exceeding 100° C. At low temperatures, a drawback is that the reaction is slow and the sugar (glucose and fructose) hydrates are crystallized, whereas at high temperatures the destruction of both the enzyme and the fructose takes place considerably more rapidly.

Continuous isomerization is typically carried out. in such a manner that the column is filled with cross-linked enzyme crystals of 100 to 300 micrometers. The size and height of the column can be varied according to the capacity required in each particular case. In a small column a suitable bed height is 5 to 50 cm. The temperature may also be varied within wide limits. Room temperature is readily realizable. If microbiological contaminations present a problem, they can be eliminated by a rising the temperature to at least about 60° C.

The process is easy to control by varying the linear flow rate. With a small column the linear flow rate ranges from 2 to 30 cm/min. A retention time suitable for fresh enzyme is 1 to 2 minutes. The pressure is atmospheric. The pressure loss is insignificant (<0.2 bar per a bed height of 50 cm). The retention time is adjusted by varying the bed height of the column and by the flow rate. The isomerization reaction can be accelerated by raising the temperature.

In a conventional industrial process, the aim is, in most cases, to obtain a sugar solution in which 40 to 45% of the sugar is fructose. When the activity of the enzyme decreases with the ageing of the column, the desired level is maintained by reducing the flow rate.

The following examples illustrate the invention more closely:

EXAMPLE 1

850 g of glucose isomerase crystal mass crystallized in a 10% ammonium sulfate solution as described in U.S. Pat. No. 4,699,882 was weighed and to said crystal mass, 1000 ml of a sulfate solution pH 7.4 (buffered by a 0.5M sodium phosphate) was added. The mixture was cooled to 10° C. The resulting mixture was stirred constantly by means of a propeller stirrer using a low speed (200 to 400 rpm), for decreasing the damaging of the crystals. A 160 ml aliquot of 25% glutaraldehyde was added to the mixture. After one hour the reaction was arrested by adding 20 liters of pure water into the mixture. The stirring was ended immediately and the crystal mass was allowed to settle on the bottom of the vessel for two hours. The mother liquor was decanted apart taking care not to flush off the crystals. 20 liters of pure water were again mixed into the crystal mass and the washing water was removed by decanting. Still another washing with water was carried out. The obtained wet isomerase crystal mass, washed three times with water, was used as such in isomerization tests, activity determinations and other experiments.

The cross-linked glucose isomerase so prepared was in a crystalline state (microscopic appreciation). The crystals were insoluble in water, dilute solutions of various salts (within the pH range of 2 to 9), dilute acids (1 mole/liter), hot water and hot salt solutions up to 100° C., and concentrated glucose, fructose and sugar solutions up to 100° C. The appearance of the crystals remained unchanged under all the above-mentioned conditions, whereas crystalline isomerase had not been cross-linked was dissolved or precipitated as an amorphous precipitate. The enzymatic activity of the cross-linked isomerase was 52% of that of the original isomerase which had not been cross-linked. That is, when the activity of the original isomerase was 40,000 GIU/g, the activity of cross-linked crystals was correspondingly more than 20,000 GIU/g, calculated per dried enzyme protein.

EXAMPLE 2

With the arrangement of Example 1, the following o reaction mixture was prepared at 25° C.:

14 g isomerase calculated as pure enzyme protein
10 g ammonium sulfate
1.5 g glutaraldehyde (about 8 ml of a 25% solution)
0.05M sodium phosphate buffer (pH of the solution 7.4)
100 ml water After a reaction time of one hour, free solution was removed from the mixture by means of a laboratory centrifuge by centrifuging at 1000 rpm for five minutes. The crystal mass obtained was suspended in 200 ml of pure water and centrifuged again as described above. Washing with water was repeated once more as described above. Wet washed crystal mass was recovered and used for further research. The activity of the crystal mass so prepared was 49% of that of the original crystal mass.

EXAMPLES 3 to 8

Reaction mixtures having the same initial composition as in Example 2 were prepared with the arrangement of Example 1 at 10° C. After reaction times of varying lengths, the reaction was arrested and the crystal mass was washed, whereafter the activity of each crystal mass was determined. The results are shown in the following Table 1.

TABLE 1

| | Reaction time | Activity (% of the activity of the original crystal mass) |
|---|---|---|
| Example 3 | 10 min | 45 |
| Example 4 | 30 min | 46 |
| Example 5 | 60 min | 49 |
| Example 6 | 90 min | 48 |
| Example 7 | 2 h | 40 |
| Example 8 | 3 h | 40 |

It can be seen from the results that the reaction is completed very rapidly and the activity does not change in any greater degree when the reaction time is increased.

EXAMPLES 9 to 16

With the arrangement of Example 1, reaction mixtures having the following initial composition were prepared at 10° C.:

14 g glucose isomerase protein (in crystalline form)
10 g ammonium sulfate
90 ml 0.5M sodium phosphate solution (pH 6.0, 7.0, 8.0 or 8.4, as shown in Table II)
glutaraldehyde 0.12, 0.5, 2.0, 3.5 or 4.12 g (as shown in Table II)

Reaction time was one hour. The activity of each resultant crystal mass (% on the original activity of the crystal mass) is shown in Table II.

TABLE II

| | pH | Glutar aldehyde (g) | Activity (%) |
|---|---|---|---|
| Example 9 | 6.0 | 0.5 | 22 |
| Example 10 | 6.0 | 3.5 | 24 |
| Example 11 | 7.0 | 0.12 | 60 |
| Example 12 | 7.0 | 2.0 | 65 |
| Example 13 | 7.0 | 4.12 | 59 |
| Example 14 | 8.0 | 0.5 | 41 |
| Example 15 | 8.0 | 3.5 | 44 |
| Example 16 | 8.4 | 2.0 | 39 |

It appears from the results that the amount of glutaraldehyde can be varied within fairly wide limits and nevertheless obtain high activities. The acidity greatly affects the result; the preferred pH value is about 7.0, though useful preparation can be obtained within the entire pH range tested, i.e., pH 6.0 to 8.4.

EXAMPLES 17 to 27

A test series similar to the preceding examples was carried out; however, the temperature was 2° C. and the reaction time 18 hours. The composition of the reaction mixture was the following:

3 g isomerase crystals calculated as dry protein
50 ml water as a medium
7.5 g salt (sodium sulfate, magnesium sulfate and/or ammonium sulfate (see Table III)
sodium hydroxide for adjusting pH to 7.0 (not more than 2 meq, that is, 80 mg)
0.125 to 2.5 g glutaraldehyde (see Table III).

TABLE III

| | (NH4)2SO4 | Salt (g) MgSO4 | Na2SO4 | Glutar-aldehyde (g) | Activity (%) |
|---|---|---|---|---|---|
| Example 17 | | | 7.5 | 0.5 | 0 |
| Example 18 | | | 7.5 | 2.5 | 0 |
| Example 19 | | 7.5 | | 0.125 | 0 |
| Example 20 | | 7.5 | | 0.5 | 0 |
| Example 21 | | 7.5 | | 0.75 | 0 |
| Example 22 | | 7.5 | | 1.25 | 0 |
| Example 23 | 0.45 | 7.05 | | 0.75 | 20 |
| Example 24 | 0.90 | 6.6 | | 0.75 | 19 |
| Example 25 | 1.8 | 5.7 | | 0.75 | 28 |
| Example 26 | 3.75 | 3.75 | | 0.75 | 40 |
| Example 27 | 7.5 | | | 0.75 | 60 |

It appears from the results that when cross-linking is carried out in the absence of an ammonium salt, insoluble crystals are not obtained, not even with a high glutaraldehyde concentration. Even a small amount of ammonium salt promotes the formation of insoluble crystals.

EXAMPLES 28-38

Insoluble isomerase crystals were prepared using various nitrogen compounds according to the following general method:

3 g crystalline isomerase calculated as dry protein
7.5 g magnesium sulfate
10 mmol nitrogen compound (see Table IV)
2.5 g glutaraldehyde (calculated as 100%)
temperature 2° C. and
reaction time 18 hours

TABLE IV

| | Nitrogen compound | Amount (g) | Activity (%) |
|---|---|---|---|
| Example 28 | lysine | 1.83 | 80 |
| Example 29 | arginine | 1.74 | 17 |

TABLE IV-continued

| | Nitrogen compound | Amount (g) | Activity (%) |
|---|---|---|---|
| Example 30 | histidine | 1.55 | 26 |
| Example 31 | glutamine | 1.46 | 18 |
| Example 32 | leucine | 1.31 | 21 |
| Example 33 | isoleucine | 1.31 | 18 |
| Example 34 | proline | 1.15 | 10 |
| Example 35 | methionine | 1.49 | 27 |
| Example 36 | phenylalanine | 1.65 | 17 |
| Example 37 | tryptophane | 2.04 | 44 |
| Example 38 | betaine | 1.17 | 23 |

It appears from the results that a number of different amines have a similar effect on the cross-linking process.

EXAMPLES 39 to 51

Insoluble isomerase crystals were prepared with different dosages of glutaraldehyde and lysine according to the following general precept:
3 g crystalline isomerase calculated as dry protein
7.5 g magnesium sulfate
0.47 to 2.34 g lycine (see Table V)
pH adjusted to 8.0 with a sodium hydroxide solution
0.5 to 1.25 g glutaraldehyde (100%; see Table V)
Solution was allowed to react 18 hours at 2° C.

TABLE V

| | Glutar aldehyde (g) | Lysine (g) | Activity (%) |
|---|---|---|---|
| Example 39 | 0.5 | 0.47 | 67 |
| Example 40 | 0.5 | 0.94 | 77 |
| Example 41 | 0.5 | 1.40 | 60 |
| Example 42 | 0.75 | 0.47 | 72 |
| Example 43 | 0.75 | 0.94 | 83 |
| Example 44 | 0.75 | 1.40 | 92 |
| Example 45 | 0.75 | 1.87 | 81 |
| Example 46 | 0.75 | 2.34 | 75 |
| Example 47 | 1.25 | 0.47 | 68 |
| Example 48 | 1.25 | 0.94 | 78 |
| Example 49 | 1.25 | 1.40 | 90 |
| Example 50 | 1.25 | 1.87 | 102 |
| Example 51 | 1.25 | 2.34 | 100 |

It appears from the results that the ratio between the dosages of lysine and glutaraldehyde affects the formation of insoluble crystals, that is, an optimum lysine dosing level is to be seen at each glutaraldehyde dosing level.

EXAMPLE 52 to 56

Isomerase crystals were cross-linked in the solutions of ammonium sulfate and lysine according to the following general precept:
10 g isomerase crystals in 10% ammonium sulfate (i.e. 3.72 g pure isomerase protein calculated as dry substance, 0.63 g ammonium sulfate and 5.65 g water)
5 g ammonium sulfate
45 g water
1.25 g glutaraldehyde calculated as 100%
0 to 3 g lysine (see Table VI) The pH of all the reaction components was adjusted to 8.0 by means of sodium hydroxide before stirring.
The mixtures were stirred at 3° C. for 18 hours.

TABLE VI

| | Lysine (g) | Activity (%) |
|---|---|---|
| Example 51 | 0 | 40 |
| Example 52 | 0.3 | 62 |

TABLE VI-continued

| | Lysine (g) | Activity (%) |
|---|---|---|
| Example 53 | 0.6 | 66 |
| Example 54 | 1.2 | 72 |
| Example 55 | 1.8 | 92 |
| Example 56 | 3.0 | 96 |

It appears from the results that lysine affects very favorably the yield of the cross-linking. Ammonium sulfate has no greater effect on the result when lysine is available, even though ammonium sulfate alone gives a satisfactory result.

EXAMPLES 57 to 68

The amount of isomerase and lysine was kept constant and the other components were varied as shown in Table VII:
3 g glucose isomerase calculated in dry form
1 g lysine
0.01 g sodium hydroxide (solution pH 8).
The reaction time was 18 and temperature 2° C.

TABLE VIII

| | Glutar aldehyde (g) | MgSO4 (g) | Water (g) | React. solution total (g) | Activity (%) |
|---|---|---|---|---|---|
| Example 57 | 0.5 | 2.1 | 11.9 | 18.5 | 39 |
| Example 58 | 0.5 | 2.7 | 15.3 | 22.5 | 70 |
| Example 59 | 0.5 | 4.2 | 23.8 | 32.5 | 70 |
| Example 60 | 0.5 | 5.3 | 32.7 | 42.5 | 73 |
| Example 61 | 0.5 | 10.2 | 57.8 | 72.5 | 75 |
| Example 62 | 0.5 | 16.2 | 91.8 | 112.5 | 77 |
| Example 63 | 1.25 | 2.1 | 11.9 | 19.25 | 86 |
| Example 64 | 1.25 | 2.7 | 15.3 | 23.25 | 99 |
| Example 65 | 1.25 | 4.2 | 23.8 | 33.25 | 101 |
| Example 66 | 1.25 | 5.3 | 32.7 | 43.25 | 89 |
| Example 67 | 1.25 | 10.2 | 57.8 | 73.25 | 83 |
| Example 68 | 1.25 | 16.2 | 91.8 | 113.25 | 89 |

It appears from the results that the concentration of the reaction mixture has little effect on the final result. The weight ratios between the reaction components (enzyme, lysine (or amine) and glutaraldehyde) have a much greater effect.

EXAMPLE 69

1 g of cross-linked glucose isomerase mass (from Example 55; 0.4 g dry substance) washed with water was mixed into 100 g of a 40% glucose solution the pH of which had been adjusted to 7.0. The mixture was stirred constantly at 60° C. Samples were taken from the mixture intermittently, and the fructose content of the samples was determined by means of a polarimeter and the glucose content measured enzymatically by means of a hexokinase. The fructose content of the solution rose to 42% on the total sugar content of the solution (glucose+fructose=100%) during 3 hours. After the test the cross-linked isomerase was separated from the mixture by filtering and was washed with water. The recovered crystal mass was tested for its activity and dry content and it was found that no active enzyme had been dissolved or disappeared in the test. The test could be repeated several times with the same enzyme batch.

EXAMPLE 70

Crystal mass prepared as described in Example 1 was washed for removing fine-grained precipitate and crystal material crushed fine during the process by suspending in water and decanting (3 times). The large crystal fraction so obtained, mean size 100 micrometres, was packed into a cylindrical reactor having a diameter of 2.6 cm and a height of 5 cm. Glucose solution having the following composition was pumped through the column at 60° C.:

582 g glucose monohydrate
596 g water
0.37 g $MgSO_4.7H_2O$
0.19 g $NaHSO_3$ pH 6.9 (1M NaOH, consumption below 1 ml) At the beginning of the test the flow rate was 11 ml/min, whereby the fructose content of the solution discharged from the column had risen to 42% on the total sugar content. The test was continued for 200 hours, whereafter the flow rate had to be reduced to 9 ml per minute for maintaining the original conversion (fructose content 42%). Accordingly, the activity of the enzyme had dropped during this period of time to 81% from the initial value. No reduction or dissolving of the crystal mass could be observed during the test.

EXAMPLES 70 to 74

43.42 g of wet active isomerase mass washed with water (prepared by the method of Example 66; 10.0 g enzyme on dry substance) was weighed.

200 ml of a glucose solution prepared as described in Example 70 was poured on the crystal mass. The mixture was shaken at 60° C. for different periods of time and the mixture was then filtered through a filter paper disc. The crystal mass remaining on the paper was washed carefully with water for removing all soluble material. The crystal mass was dried in an incubator at 105° C. and weighed. The observations are presented in the following Table VIII:

TABLE VIII

| | Stirring time | Dry weight of crystal mass after test (g) |
|---|---|---|
| Example 70 | 10 min | 9.9 |
| Example 71 | 2 h | 11.0 |
| Example 72 | 4 h | 10.9 |
| Example 73 | 6 h | 10.7 |
| Example 74 | 21 h | 10.4 |

It appears from the results that the cross-linked crystalline isomerase prepared by the process according to the invention does not dissolve in the substrate under conventional industrial operating conditions.

EXAMPLE 75

Cross-linked, crystalline isomerase, isomerase bound to DEAE cellulose and original free soluble isomerase were compared with each other by keeping them under identical chemical and physical conditions. The conditions were chosen so that each enzyme sample lost its activity to a measurable extent in a reasonably short time, i.e., in 10–30 hours. A 5 g portion of each enzyme preparation was mixed into 150 ml 0.05M sodium phosphate buffer (pH 6.0), which further contained 1.5 mmol/liter $MgSO_4$ and 2 mmol/liter $NaHSO_3$. The mixture was shaken for several hours at 70° C. Samples were taken intermittently from the mixture, and the activity of the remaining isomerase was determined from the samples. The half-value time of each enzyme sample (i.e., the time period during which the activity drops to one half of the original value) was determined on the basis of the activity decrease. The results are shown in the following Table IX.

TABLE IX

| Enzyme sample | Half-time (h) |
|---|---|
| Original soluble isomerase | 2.2 |
| Isomerase bound to DEAE cellulose | 3.3 |
| Cross-linked crystalline isomerase | 19.0 |

It appears from the results that cross-linked crystals retain their enzymatic activity substantially better than a free enzyme or an enzyme immobilized in a known manner.

EXAMPLE 76

Cross-linked crystalline isomerase and isomerase bound to DEAE cellulose were packed into a cylindrical column reactor similarly as described in Example 70. Glucose solution was pumped continuously through the columns. The glucose solution had the same composition as in Example 70 except that the pH was adjusted to 6.0. The temperature of the columns was 60° C. during the test. The activity of the enzyme contained in the columns was calculated on the basis of the flow rate and the fructose content of the solution which has flown through. The results are shown in the following Table X.

TABLE X

| Reactor packing | Activity half-time (h) |
|---|---|
| Cross-linked isomerase crystal mass | 120 |
| Isomerase bound to DEAE cellulose | 36 |

It appears from the results that cross-linked crystals retain their enzymatic activity excellently.

EXAMPLE 77

Samples of typical industrially used isomerases and the crosslinked crystals of this invention were packed into similar laboratory columns. Crosslinking of the crystals was performed as described in Example 51. The inside diameter of the cylindrical columns was 2.7 cm and height 50 cm. The columns were water jacket thermostated to 60° C. The lower end of the vertical columns had a screen to keep the enzyme granules in the column and to let the sugar solution flow through. Twenty grams (on a dry substance basis) of each enzyme was poured into the individual columns. Glucose substrate having the composition as in Example 70 was pumped with an adjustable laboratory pump through the columns. Each column had an individual pump. The temperature of the substrate was adjusted to 60° C. The product coming through the column was assayed for fructose and glucose content. It was observed that each different enzyme preparation produced a different content of fructose when the substrate flow rate was similar. The flow rate of each column was adjusted individually by trial and error until the fructose content of each product was 45 percent of total sugars (glucose in fructose). The following table lists the enzymes and corresponding flow rates to produce 45 percent fructose.

TABLE XI

| Enzyme (20 g dry substance) | Substrate Flow (milliters per hour) |
|---|---|
| SPEZYME IGI, commercial product of Finnish Sugar Co. | 179 |
| SWEETZYME T, commercial product of NOVO Co. Denmark | 197 |
| TAKASWEET, commercial | 94 |

TABLE XI-continued

| Enzyme (20 g dry substance) | Substrate Flow (milliters per hour) |
| --- | --- |
| product of Miles-Kali Chemie | |
| Crosslinked isomerase crystals of diameter 100–200 micrometers | 1364 |
| Crosslinked isomerase crystals of diameter 500–600 micrometers | 1121 |
| Crosslinked isomerase crystals of diameter 900–1100 micrometers | 1098 |

The flow rates of the commercial samples represent what is typically observed in present industrial practice. The flow rates of the crystal columns were substantially higher. In industrial practice, the high activity of cross-linked crystals will result in essentially small enzyme columns, which will give savings in investment and processing costs.

I claim:

1. A process for the preparation of a cross-linked crystalline glucose isomerase, the cross-linked crystalline glucose isomerase characterized by maintaining high enzymatic activity and being insoluble in water, salt solutions or sugar solutions, the process comprising:
   a) adding to a crystalline glucose isomerase suspension a compound containing at least one amino group, said compound selected from the group consisting of an ammonium salt, lysine and tryptophan, said compound being added at a concentration of between about 1% and about 15% and at a pH of about 7.0 to about 8.4;
   b) adding glutaraldehyde to initiate a cross-linking reaction;
   c) continuing the cross-linking reaction until cross-linking occurs; and
   d) separating and washing the cross-linked product of step c) with water or a suitable salt solution.

2. a process according to claim 1 wherein the compound is lysine.

3. A process according to claim 1, wherein the amount of glutaraldehyde is about 0.4 to about 8 percent by weight.

4. A process according to claim 1, wherein the amount of glutaraldehyde is about 1 to about 45% by weight of wet crystal mass.

* * * * *